(12) United States Patent
Bröcker et al.

(10) Patent No.: US 6,278,031 B1
(45) Date of Patent: Aug. 21, 2001

(54) CATALYST AND PROCESS FOR PREPARING 2-BUTEN-1-OL COMPOUNDS

(75) Inventors: Franz Josef Bröcker, Ludwigshafen; Werner Aquila, Mannheim; Klemens Flick, Herxheim; Gerd Kaibel, Lampertheim; Ernst Langguth, Kirchheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/759,688

(22) Filed: Jan. 16, 2001

Related U.S. Application Data

(62) Division of application No. 08/957,322, filed on Nov. 6, 1997.

(30) Foreign Application Priority Data

Nov. 12, 1996 (DE) .............................................. 196 46 679

(51) Int. Cl.$^7$ .................................................. C07C 27/00
(52) U.S. Cl. ................... 568/906; 560/113; 560/261; 568/450; 568/675; 568/687; 568/825; 568/838; 568/857; 568/875
(58) Field of Search .................................... 568/906, 450, 568/675, 687, 825, 838, 857, 875; 560/113, 261

(56) References Cited

U.S. PATENT DOCUMENTS

| | | |
|---|---|---|
| 3,697,580 | 10/1972 | Oversien . |
| 3,755,423 | 8/1973 | Onoda . |
| 3,864,281 | 2/1975 | Ohorodnik . |
| 4,122,291 | 10/1978 | Kyo . |
| 4,310,709 | 1/1982 | Rebafka . |
| 5,189,202 * | 2/1993 | Kim ..................................... 560/213 |
| 5,777,155 | 7/1998 | Sato . |

FOREIGN PATENT DOCUMENTS

| | | |
|---|---|---|
| 1901709 | 8/1970 | (DE) . |
| 2751766 | 5/1979 | (DE) . |
| 2725965 | 5/1983 | (DE) . |
| 647611 | 4/1995 | (EP) . |
| 2196196 | 3/1974 | (FR) . |
| 2053959 | 2/1981 | (GB) . |

OTHER PUBLICATIONS

McGreer et al., *Canadian J. of Chem.*, 46, 1968, 2225–2232.
Goetz et al., *J. Am. Chem. Soc.*, 85, 1963, 1549–1550.

* cited by examiner

Primary Examiner—Michael L. Shippen
(74) Attorney, Agent, or Firm—Keil & Weinkauf

(57) ABSTRACT

The fixed-bed catalyst comprises palladium and selenium or tellurium or a mixture of selenium and tellurium on a silicon dioxide support and has a BET surface area of from 80 to 380 m$^2$/g and a pore volume of from 0.6 to 0.95 cm$^3$/g in the pore diameter range from 3 nm to 300 μm, with from 80 to 95% of the pore volume being in the pore diameter range from 10 to 100 nm.

It is prepared by impregnating a silicon dioxide support with a solution of a palladium compound and a selenium compound or tellurium compound or a mixture of a selenium compound and a tellurium compound, drying it and reducing it in the presence of hydrogen.

The catalyst is used, in particular, for isomerizing 3-buten-1-ol compounds.

5 Claims, No Drawings

CATALYST AND PROCESS FOR PREPARING 2-BUTEN-1-OL COMPOUNDS

This is a Divisional application of application Ser. No. 08/957,322, filed Nov. 6, 1997 (allowed).

The present invention relates to a fixed-bed catalyst and a continuous process for preparing 2-buten-1-ol compounds.

J. Am. Chem. Soc., 85 (1963), pages 1549 to 1550 discloses the isomerization of an unsaturated alcohol using a carbonyl compound of a metal from group VIII of the Periodic Table of Elements as catalyst. This process gives numerous by-products and secondary products, for example the corresponding aldehydes.

Can. Journ. of Chem., 46 (1968), 2225 to 2232 discloses the thermal isomerization of unsaturated alcohols in the absence of a catalyst. At the high temperatures required, the starting compounds are partly converted to resin.

DE-C-19 01 709 describes a process for preparing buten-2-ol-4 compounds in which buten-1-ol-4 compounds are reacted in the presence of palladium or palladium compounds, for example palladium/carbon, and hydrogen.

However, when using pure palladium in the presence of hydrogen, significant hydrogenation of the double bond of the compounds occurs and a saturated product is formed. In addition, low-boiling compounds such as hydrocarbons and aldehydes are formed as by-products, for example by hydrogenolysis and isomerization. The hydrogenation of the double bond is undesired since in the case of some butenols there are only small boiling point differences between unreacted starting material and hydrogenation product. Thus, the boiling point of 3-methyl-3-buten-1-ol, for example at 1020 mbar, is 131.5° C. while the boiling point of the corresponding hydrogenation product 3-methyl-1-butanol is 130.9° C. This makes it difficult to separate hydrogenation product and starting material by distillation.

DE-C-27 25 965 discloses a process for preparing a 2-alken-1-ol in which a 3-alken-1-ol is converted into the boric ester of the alkenol, the isomerization is subsequently carried out in the presence of a palladium catalyst, e.g. palladium on activated carbon, and hydrogen and the resulting reaction mixture is subjected to solvolysis. Fewer by-products are formed as a result of the hydroxyl group of the 3-alken-1-ol being protected by esterification. However, additional process steps are necessary.

DE-A-27 51 766 discloses a process for isomerizing 3-buten-1-ol compounds to give the corresponding 2-buten-1-ol compounds, with the isomerization being carried out in the presence of palladium and selenium or tellurium as catalyst and hydrogen. The catalyst used is palladium and selenium on activated carbon. As further usable supports, mention is made of barium sulfate, silica gel, aluminum oxide and zeolites. The catalysts can also be used without supports. Relatively high proportions of low boilers such as isoprene and methylbutenes are formed.

The known catalytic isomerizations are carried out batchwise, for example in a stirred reactor using the suspension method.

However, since the double-bond isomerization of substituted butenols is an equilibrium reaction, complete conversions are not obtained but part of the starting material always remains and for further use has to be separated from by-products formed. To carry out the isomerization in a more economical way, the reaction should be able to be carried out continuously and lead to a minimum proportion of hydrogenation products or low boilers.

It is an object of the present invention to provide a catalyst and a process for the continuous preparation of 2-buten-1-ol compounds by isomerization of 3-buten-1-ol compounds such that the proportion of hydrogenation products and low boilers obtained is very low.

We have found that this object is achieved by a fixed-bed catalyst which comprises palladium and selenium or tellurium or a mixture of selenium and tellurium on a silicon dioxide support and has a BET surface area of from 80 to 380 m²/g and a pore volume of from 0.6 to 0.95 cm³/g in the pore diameter range from 3 nm to 300 µm, with from 80 to 95% of the pore volume being in the pore diameter range from 10 to 100 nm.

The object is also achieved by use of the catalyst as an isomerization catalyst and by a process for preparing 2-buten-1-ol compounds of the formula (I)

$$H_2R^1C-R^2C=CR^3-CR^4R^5-OR^6 \qquad (I)$$

where the individual radicals $R^1$, $R^2$, $R^3$, $R^4$, $R^5$ and $R^6$ can be identical or different and are each hydrogen or an aliphatic radical which may be unsubstituted or substituted by OH, OR where R is aliphatic, halogen or carboxyl, furthermore $R^2$ can also be the radical —CHO, $R^2$ and $R^5$ together with the carbon atoms located between them can also be parts of an alicyclic ring, and $R^6$ can also be a cycloaliphatic, araliphatic, aromatic radical or the radical —C(=O)—$R^7$, where $R^7$ is an aliphatic, cycloaliphatic, araliphatic or aromatic radical, by isomerizing 3-buten-1-ol compounds of the formula (II)

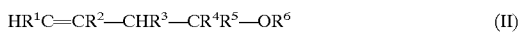

$$HR^1C=CR^2-CHR^3-CR^4R^5-OR^6 \qquad (II)$$

where $R^1$, $R^2$, $R^3$, $R^4$, $R^5$ and $R^6$ are as defined above, in the presence of hydrogen and a catalyst, wherein the process is carried out continuously over the fixed-bed catalyst described above.

The catalyst preferably contains from 0.1 to 2.0% by weight of palladium and from 0.01 to 0.2% by weight of selenium, tellurium or a mixture of selenium and tellurium, based on the total weight of the catalyst.

The BET surface area is preferably from 100 to 150 m²/g, in particular from 110 to 130 m²/g. The BET surface area is determined by $N_2$ adsorption in accordance with DIN 66131.

The pore volume in the pore diameter range from 3 nm to 300 µm is preferably from 0.8 to 0.9 cm³/g, in particular from 0.8 to 0.85 cm³/g. From 80 to 95%, preferably from 85 to 93%, of this pore volume are in the pore diameter range from 10 to 100 nm. The pore volume is determined by Hg porosimetry.

The catalyst preferably contains from 0.2 to 0.8% by weight, in particular from 0.4 to 0.6% by weight, of palladium. The catalyst preferably contains from 0.02 to 0.08% by weight, in particular from 0.04 to 0.06% by weight, of selenium, tellurium or a mixture of selenium and tellurium, preferably selenium.

Apart from the active components mentioned, further metals may be present on the catalysts in small amounts. Preferably, only palladium, selenium and/or tellurium, in particular only palladium and selenium, are present on the silicon dioxide support.

The catalysts of the present invention can be prepared by any suitable methods. They are preferably prepared by impregnation of a silicon dioxide support with a solution of a palladium compound and a selenium compound or tellurium compound or a mixture of a selenium compound and a tellurium compound. It is here possible to use one or more palladium compounds, selenium compounds and/or tellurium compounds. Preference is given to using the compounds in the form of aqueous solutions. In such solutions, palladium is preferably used in the form of salts such as palladium nitrate or complexes. Selenium and/or tellurium are used, for example, in oxidic form. Further suitable palladium, selenium and tellurium compounds are described in DE-A-27 51 766. The silicon dioxide support can be impregnated in succession with solutions of the individual compounds in any order, with the catalyst support being able to be dried between the individual impregnation steps. However, the catalyst support can also be impregnated with a solution in which the compounds of the active substances are present in an appropriate desired ratio. The concentration of the solutions can be selected such that the desired amount of palladium and selenium and/or tellurium can be applied to the catalyst by means of a single impregnation. However, application by multiple impregnation is also possible.

The catalyst support is preferably agitated in the solution of the active substances, and the impregnated catalyst is then dried at about 120° C. and subsequently heat treated at about 200° C. Before or during use of the catalyst in the isomerization, the active substances, ie. palladium and selenium and/or tellurium, are reduced in the presence of hydrogen.

The catalyst support is preferably prepared by precipitating silicon dioxide from an alkali metal silicate solution and then drying it and pressing it to form shaped bodies, and subsequently calcining the shaped bodies thus produced at from 400 to 1100° C., preferably from 600 to 900° C., in particular from 800 to 900° C.

This may be carried out, for example, by placing aqueous ammoniacal alkali metal silicate solution in a vessel and treating it with aqueous sulfuric acid so that silicon dioxide is precipitated. The resulting precipitate can then be filtered off, washed and spray dried. The spray drying is preferably carried out in such a way that the silicon dioxide powder obtained has a water content corresponding to a loss on ignition of from 25 to 35% by weight on ignition at 900° C. for 2 hours. The silicon dioxide powder obtained can then be mixed into a paste using a peptizing agent and brought into the desired shape. When used as fixed-bed catalyst, this can have all suitable macroscopic shapes, for example in the form of extrudates, tablets, pellets of any shape, spheres or rings. The silicon dioxide powder is preferably extruded. The extrudates are then dried at 120 to 150° C. and subsequently calcined at from 400 to 1100° C., preferably from 600 to 900° C., in particular from 800 to 900° C.

Other methods of preparation can also be selected for the silicon dioxide supports, as long as the supports obtained have the indicated BET surface area, pore size and pore size distribution.

The isomerization of the present invention can be carried out in any apparatus in which it is possible to carry out a process continuously. The isomerization is preferably carried out in the upflow mode in a tube reactor containing the fixed-bed catalyst of the present invention. The tube reactor preferably contains a gas distributor in the lower part, for example in the form of a filter plate, a static mixer or a nozzle. The gas distributor serves to feed in hydrogen which is preferably distributed uniformly across the reactor cross section. The 3-buten-1-ol compound to be isomerized is introduced into the reactor from below and treated with hydrogen. The space velocity over the catalyst is set such that a conversion of preferably from 45 to 65%, particularly preferably from 50 to 60%, is achieved at the reactor outlet. The introduction of hydrogen is set as a function of temperature and total pressure in such a way that a hydrogen partial pressure of from 0.5 to 5 bar, preferably from 0.5 to 2 bar, in particular from 0.6 to 1 bar, is maintained. The hydrogen which has passed through the reactor can be discharged as waste gas after condensing out low boilers or can be recirculated to the process.

The isomerization is carried out at from 50 to 120° C., preferably from 80 to 100° C. Depending on the starting compound used, space velocities of the catalyst of from 0.5 to 5 l/l(catalyst)×h, preferably from 0.5 to 1.5 l/l(catalyst)×h, are employed.

The reaction product mixture obtained from the equilibrium reaction is preferably passed directly to work-up by distillation. Here, the unreacted starting material is isolated and returned to the isomerization. The separation by distillation of the reaction product from the starting material and the return of the starting material are necessary for carrying out the isomerization process economically. The separation by distillation is preferably carried out continuously in suitable apparatuses.

The process of the present invention can be carried out in the presence or absence of an inert organic solvent. Inert organic solvents which can be used are, for example, ethers such as diethyl ether, dioxane or tetrahydrofuran, alcohols such as ethanol or isobutanol, aromatic or aliphatic hydrocarbons such as heptane or benzene or mixtures thereof. Preference is given to carrying out the process without an inert organic solvent.

Starting Materials

According to the present invention, the 2-buten-1-ol compounds of the formula (I)

$$H_2R^1C-R^2C=CR^3-CR^4R^5-OR^6 \qquad (I)$$

where the individual radicals $R^1$, $R^2$, $R^3$, $R^4$, $R^5$ and $R^6$ can be identical or different and are each hydrogen or an aliphatic radical which may be unsubstituted or substituted by OH, OR where R is aliphatic, halogen or carboxyl, furthermore $R^2$ can also be the radical —CHO, $R^2$ and $R^5$ together with the carbon atoms located between them can also be parts of an alicyclic ring and $R^6$ can also be a cycloaliphatic, araliphatic, aromatic radical or the radical —C(=O)—$R^7$, where $R^7$ is an aliphatic, cycloaliphatic, araliphatic or aromatic radical, are prepared using 3-buten-1-ol compounds of the formula (II)

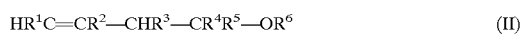

$$HR^1C=CR^2-CHR^3-CR^4R^5-OR^6 \qquad (II)$$

where $R^1$, $R^2$, $R^3$, $R^4$, $R^5$ and $R^6$ are as defined above.

Preferably, the radicals $R^1$, $R^2$, $R^3$, $R^4$, $R^5$ and $R^6$ are identical or different and are each hydrogen or a $C_1$–$C_{12}$-, preferably $C_1$–$C_6$-alkyl radical which may be unsubstituted or substituted as described above. They are particularly preferably hydrogen or methyl.

According to one embodiment, $R^2$ and $R^5$ together with the carbon atoms located between them form parts of a 5-, 6- or 7-membered alicyclic ring. $R^6$ can be a cycloalkyl radical having from 5 to 7 carbon atoms, an aralkyl radical having from 7 to 12 carbon atoms, a phenyl radical, naphthyl radical or the radical —C(=O)—$R^7$, where $R^7$ is a $C_1$–$C_{12}$-, preferably $C_1$–$C_6$-alkyl radical, a $C_5$–$C_7$-cycloalkyl radical, a $C_7$–$C_{12}$-aralkyl radical, a phenyl radical or naphthyl radical. The radicals mentioned can also be substituted by groups and/or atoms which are inert under the reaction conditions, for example ether groups such as ethylene oxide units.

Preferred examples of compounds of the formula (II) which can be used according to the present invention are 3-buten-1-ol, 3-methyl-3-buten-1-ol, 4-formyl-3-buten-1-ol, 3,2,1-trimethyl-3-buten-1-ol, 2-isobutyl-3-buten-1-ol, 3-(2'- hydroxyethyl)-3-buten-1-ol, 1-hexyl-3-buten-1-ol, 1-methylene-2-methylcyclohexan-3-ol, 1-methylene-2-ethylcyclopentan-3-ol, 1-methylenecyclohexan-3-ol, 1-methylenecycloheptan-3-ol, and also the corresponding ethyl, cyclohexyl, benzyl, phenyl and α-naphthyl ethers or the corresponding acetic, cyclohexanecarboxylic, benzoic, α-naphthoic or dihydrocinnamic esters.

Particular preference is given to using 3-methyl-3-buten-1-ol and its derivatives which are substituted on the oxygen, e.g. acetates or ethers, in the process of the present invention.

The invention is illustrated by the examples below.

EXAMPLE 1

Catalyst Preparation

A stirred reactor is charged with an aqueous ammoniacal sodium silicate solution and, while stirring, silicon dioxide is precipitated using aqueous sulfuric acid. The precipitate obtained is filtered off, washed and subsequently spray dried. Spray drying is carried out in such a way that the resulting silicon dioxide powder has a water content which corresponds to a loss on ignition of from 25 to 35% by weight in 2 hours at 900° C. The silicon dioxide powder thus obtained is mixed into a paste with water and ammonia as peptizing agent and extruded to give extrudates having a diameter of 3 mm. The extrudates are dried in a drying oven at from 120 to 150° C. and subsequently calcined at from 820 to 870° C.

300 g of the resulting support material in the form of extrudates having a diameter of 3 mm are admixed in a round-bottom flask on a rotary evaporator with an aqueous solution of 13.64 g of palladium nitrate solution containing 11% by weight of palladium and 0.21 g of $SeO_2$ in 244 g of distilled water. The flask is rotated at room temperature until the entire solution has been absorbed by the support material. The flask containing the catalyst is subsequently heated to 120° C. while continuing the rotation and the contents are dried in 3 hours at a rotational speed of 9 revolutions per minute while passing in 2000 l of air per hour. After drying, the temperature is increased to 200° C. while rotating the flask continually and passing in 1000 l of air/h and the catalyst is heat-treated for 3 hours.

The silicon dioxide supported catalyst thus obtained contains 0.5% by weight of palladium and 0.05% by weight of selenium, based on the total weight of the catalyst. The BET surface area is 119 m²/g and the pore volume is 0.82 cm³/g in the pore diameter range from 3 nm to 300 μm. Of this pore volume, 91.7% is in the pore diameter range from 10 to 100 nm.

EXAMPLE 2

100 ml of the catalyst prepared as described in Example 1 are installed in a tube reactor having jacket heating and an internal diameter of 21 mm. 3-Methyl-3-buten-1-ol from a reservoir is pumped into the reactor from below by means of a feed pump. Hydrogen is metered into the feed stream before the reactor inlet and distributed uniformly across the reactor cross section by means of a glass frit. The isomerization temperature is set to 100° C. via the reactor jacket by means of a thermostat. Hydrogen is metered in in an amount of 2.6 l/h. The total pressure in the reactor is 1.1 bar. At a space velocity of 1.0 l/l(catalyst)×h, a conversion of 55% and a selectivity of 91.5% are achieved.

EXAMPLE 3

The procedure of Example 2 is repeated, but the isomerization is carried out at 90° C., a space velocity over the catalyst of 0.9 l/l(catalyst)×h and a hydrogen feed rate of 3 l/h. At a conversion of 75%, the selectivity is 93%.

EXAMPLE 4

The procedure of Example 2 is repeated, but the isomerization is carried out at 80° C., a space velocity over the catalyst of 0.9 l/l(catalyst)×h and a hydrogen feed rate of 3.8 l/h. At a conversion of 55%, the selectivity is 93%.

EXAMPLE 5

In a long-term test over 1600 hours, the procedure described in Example 2 is repeated using 60 ml of the catalyst prepared as described in Example 1, a temperature of 90° C., a space velocity over the catalyst of 0.72 l/l (catalyst)×h and a hydrogen feed rate of 5 l/h. The conversion remains stable at 58% and the selectivity is 92%.

The results above demonstrate that the process of the present invention can be carried out continuously with high selectivities and high conversions. Even over long reaction times, conversion and selectivity remain stable. The continuous isomerization can be followed by a continuous separation by distillation of the reaction product from the starting material and the return of the starting material to the isomerization, so that the overall isomerization can be carried out economically and advantageously.

We claim:

1. A process for preparing a 2-buten-1-ol compound of formula (I)

where the individual radicals $R^1$, $R^2$, $R^3$, $R^4$, $R^5$ and $R^6$ are identical or different and are each hydrogen or an aliphatic radical which is unsubstituted or substituted by OH, OR where R is an aliphatic group, halogen or carboxyl, furthermore $R^2$ represents a radical —CHO, or $R^2$ and $R^5$ together with the carbon atoms located between them form an alicyclic ring, and $R^6$ additionally represents a cycloaliphatic, araliphatic, aromatic radical or a radical —C(=O)—$R^7$, where $R^7$ is an aliphatic, cycloaliphatic, araliphatic or aromatic radical, which process comprises isomerizing a 3-buten-1-ol compound of formula (II)

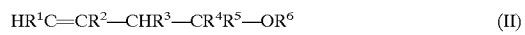

where $R^1$, $R^2$, $R^3$, $R^4$, $R^5$ and $R^6$ are as defined above, in the presence of hydrogen and a catalyst, wherein the process is carried out continuously over a fixed-bed catalyst, wherein the catalyst comprises palladium and selenium or tellurium or a mixture of selenium and tellurium on a silicon dioxide support, and has a BET surface area of from 80 to 380 m²/g and a pore volume of from 0.6 to 0.95 cm³/g in a pore diameter range of from 3 nm to 300 μm, with from 80 to 95% of the pore volume being in the pore diameter range of from 10 to 100 nm.

2. The process of claim 1, which is carried out in an upflow mode in a tube reactor.

3. The process of claim 1, wherein the compound of formula (II) is 3-methyl-3-buten-1-ol.

4. The process of claim 1, wherein the fixed-bed catalyst consists essentially of from 0.1 to 2% by weight of palladium and from 0.01 to 0.2% by weight of selenium, based on the total weight of the catalyst, on a silicon dioxide support, and has a pore volume of from 0.8 to 0.9 cm³/g in the pore diameter range from 3 nm to 300 μm.

5. The process of claim 1, wherein the fixed-bed catalyst has a BET surface area of from 100 to 150 m²/g and a pore volume of from 0.8 to 0.9 cm³/g in the pore diameter range from 3 nm to 300 μm, with from 85 to 93% of the pore volume being in the pore diameter range from 10 to 100 nm, and contains from 0.2 to 0.8% by weight of palladium and from 0.02 to 0.08% by weight of selenium, based on the total weight of the catalyst.

* * * * *